(12) United States Patent
Morita

(10) Patent No.: US 11,615,521 B2
(45) Date of Patent: Mar. 28, 2023

(54) DEFECT INSPECTION SYSTEM, DEFECT INSPECTION METHOD, AND DEFECT INSPECTION PROGRAM FOR WOOD PLANK

(71) Applicant: Meinan Machinery Works, Inc, Obu (JP)

(72) Inventor: Koji Morita, Obu (JP)

(73) Assignee: MEINAN MACHINERY WORKS, INC., Aichi (JP)

( * ) Notice: Subject to any disclaimer, the term of this patent is extended or adjusted under 35 U.S.C. 154(b) by 0 days.

(21) Appl. No.: 17/335,722

(22) Filed: Jun. 1, 2021

(65) Prior Publication Data
US 2022/0051392 A1 Feb. 17, 2022

Related U.S. Application Data

(63) Continuation of application No. PCT/JP2020/030797, filed on Aug. 13, 2020.

(51) Int. Cl.
*G06T 7/00* (2017.01)
*G01N 21/359* (2014.01)
(Continued)

(52) U.S. Cl.
CPC ......... *G06T 7/0004* (2013.01); *G01N 21/359* (2013.01); *G01N 21/95* (2013.01);
(Continued)

(58) Field of Classification Search
CPC ......... G06T 7/0004; G06T 2207/10024; G06T 2207/30161; G01N 33/46; G01N 21/95;
(Continued)

(56) References Cited

U.S. PATENT DOCUMENTS

| 5,517,580 | A | * | 5/1996 | Markandey | G01N 25/72 |
| | | | | | 348/E5.09 |
| 5,960,104 | A | * | 9/1999 | Conners | G06V 10/28 |
| | | | | | 382/141 |

(Continued)

FOREIGN PATENT DOCUMENTS

| CN | 103884650 A | * | 6/2014 |
| CN | 103884650 A | | 6/2014 |

(Continued)

OTHER PUBLICATIONS

European Search Report dated Dec. 2, 2021 issued in counterpart Patent Application No. 21177280.1 (10 pages).
(Continued)

*Primary Examiner* — Richard A Hansell, Jr.
(74) *Attorney, Agent, or Firm* — Polsinelli PC

(57) ABSTRACT

A light 2 for reflected light that emits visible light for reflected light onto a front side of a veneer 6, a light 32 for invisible light that emits near-infrared light for transmitted light onto a back side of the veneer 6, and an image processing device 1 that detects defects of the veneer 6 by analyzing a captured image generated by a line sensor camera 4 are provided. Defects of the veneer 6 are discriminated on the basis of a set of shading and shapes in an infrared-transmitted-light image based on the transmitted light, and colors in a visible-light image based on the reflected light. Consequently, even if a defect has a small color difference from a normal part in the visible-light image, difference of shading between the defective part and the normal part appears in the infrared-transmitted-light image, and a defect that is difficult to detect by seeing only a color difference in a visible-light image can be relatively easily detected.

18 Claims, 3 Drawing Sheets

(51) Int. Cl.
*G01N 21/95* (2006.01)
*G01N 33/46* (2006.01)
*H04N 5/225* (2006.01)

(52) U.S. Cl.
CPC .......... *G01N 33/46* (2013.01); *H04N 5/2256* (2013.01); *G01N 2201/062* (2013.01); *G06T 2207/10024* (2013.01); *G06T 2207/30161* (2013.01)

(58) Field of Classification Search
CPC .......... G01N 21/359; G01N 2201/062; H04N 5/2256
See application file for complete search history.

(56) References Cited

U.S. PATENT DOCUMENTS

| | | | |
|---|---|---|---|
| 6,757,058 | B1 | 6/2004 | Carman et al. |
| 8,253,793 | B2 * | 8/2012 | Hiraoka ................ B27G 1/00 348/91 |
| 10,933,556 | B2 * | 3/2021 | Bolton .................... H04N 5/33 |
| 2006/0262972 | A1 | 11/2006 | Hiraoka |
| 2010/0100275 | A1 * | 4/2010 | Mian .................. G01M 17/013 382/284 |
| 2010/0141754 | A1 * | 6/2010 | Hiraoka ............. G01N 21/8986 348/93 |
| 2011/0025838 | A1 | 2/2011 | Ninomiya |
| 2014/0038316 | A1 * | 2/2014 | Fulle ...................... H01L 22/24 250/341.4 |
| 2020/0219248 | A1 * | 7/2020 | Kaneko ............. G01N 21/8851 |
| 2021/0010944 | A1 * | 1/2021 | Prakapenka ....... G01N 21/9505 |

FOREIGN PATENT DOCUMENTS

| | | | | |
|---|---|---|---|---|
| CN | 104007116 | A | | 8/2014 |
| DE | 102016011497 | A1 * | 3/2018 | ......... G01N 21/8806 |
| EP | 2 065 676 | A1 | | 6/2009 |
| JP | S64-80535 | A | | 3/1989 |
| JP | 2006-153633 | A | | 6/2006 |
| JP | 2007-040913 | A | | 2/2007 |
| JP | 2007-147442 | A | | 6/2007 |
| JP | 2007147442 | A | * | 6/2007 |
| JP | 2011-033449 | A | | 2/2011 |
| JP | 2014-020910 | A | | 2/2014 |
| JP | 2014-190797 | A | | 10/2014 |
| JP | 2019-190891 | A | | 10/2019 |
| JP | 2019190891 | A | * | 10/2019 ......... G01N 21/3151 |
| KR | 102108724 | B1 * | 5/2020 |  |
| RU | 2730407 | C1 * | 8/2020 |  |
| WO | 97/04299 | A1 | | 2/1997 |
| WO | WO-2021229446 | A2 * | 11/2021 |  |

OTHER PUBLICATIONS

Chinese Office Action dated Oct. 25, 2021 issued in corresponding Patent Application No. 202110522912.5 (8 pages).

* cited by examiner

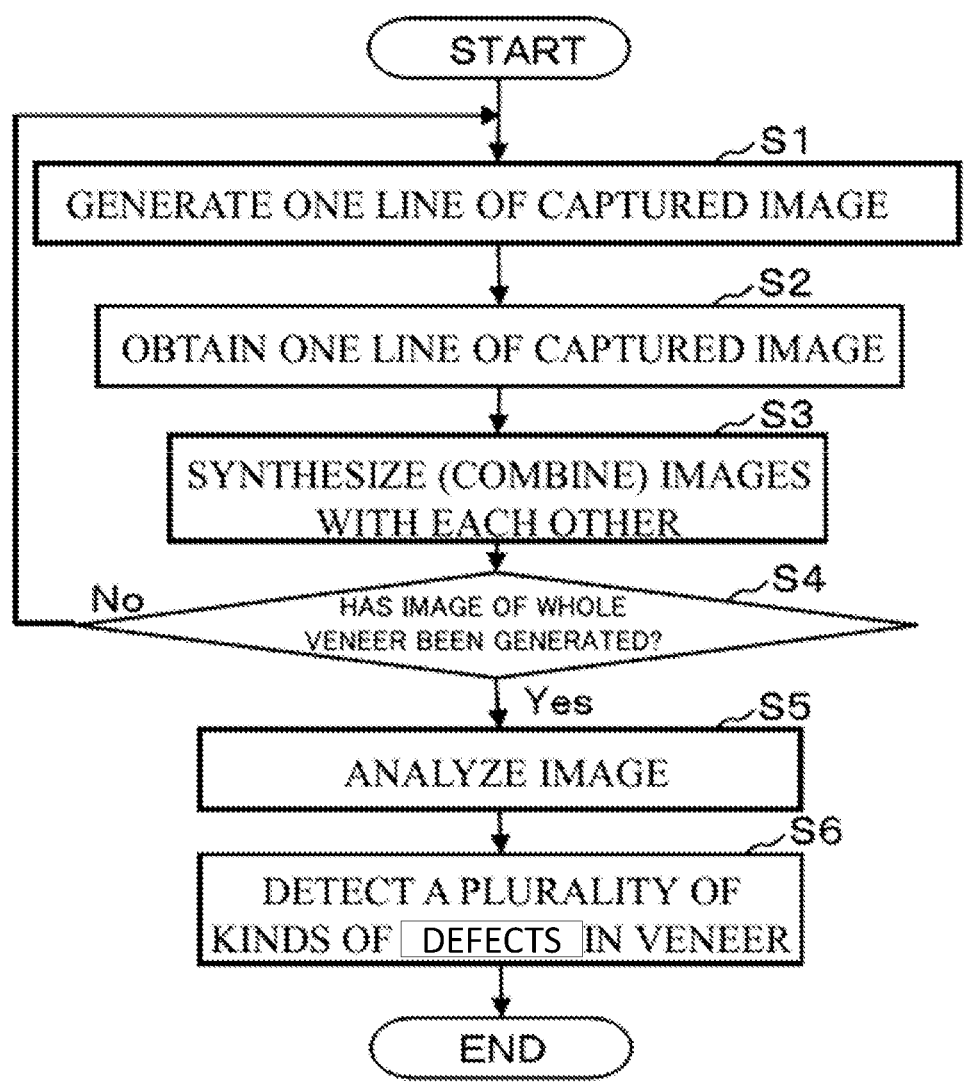

DEFECT INSPECTION SYSTEM, DEFECT INSPECTION METHOD, AND DEFECT INSPECTION PROGRAM FOR WOOD PLANK

CROSS REFERENCE TO RELATED APPLICATIONS

This application is a continuation of Application No. PCT/JP2020/030797 filed on Aug. 13, 2020, the entire contents of which are hereby incorporated by reference.

TECHNICAL FIELD

The present invention relates to a defect inspection system, a defect inspection method, and a defect inspection program for a wood plank, and is particularly suitably used for a system of detecting defects that exist in a wood plank, such as a veneer or a sawn timber sawn from a log or the like.

BACKGROUND ART

A defect inspection device that captures a timber, such as a veneer, with capture means, and uses a color distribution in a captured image to detect defective parts on the basis of discolorations on a surface of the timber has been known (for example, refer to Patent Literature 1). The defect inspection device disclosed in Patent Literature 1 emits white visible light from a light for reflected light disposed on a front side of a veneer, and emits visible light having a color that is different from the light for reflected light (for example, green) from a light for transmitted light disposed on a back side of the veneer. Then, the defect inspection device disclosed detects defects such as live knots, dead knots, and discolored part due to mold, on the basis of a captured image based on reflected light, and detects defects of a veneer, such as worm holes and cracks, on the basis of a captured image based on transmitted light.

Note that, for example, Patent Literatures 2 to 4 disclose that although a veneer is not inspected for defects, defects are detected by using transmitted light when infrared light is emitted onto an inspection object.

Patent Literature 1: JP 2007-147442 A
Patent Literature 2: JP 2006-153633 A
Patent Literature 3: JP 2011-33449 A
Patent Literature 4: JP 2014-190797 A

SUMMARY OF INVENTION

Technical Problem

However, there is a problem that some defects are difficult to detect by seeing only a color difference (difference in color) in an image captured while visible light is emitted, as is the case with the defect inspection device disclosed in Patent Literature 1. That is to say, it is difficult to detect, from a captured image based on reflected light, defects such as a live knot, a dead knot, and discolored part that is slightly discolored due to staining fungi and the like, which have a small color difference from a color of a normal part of a plank. Further, defects, such as a worm hole that does not extend through a veneer from a front side of the veneer to a back side of the veneer along a direction in which visible light is emitted, a worm hole filled with feces, and a crack that does not have openings, are difficult to detect on the basis of a captured image based on transmitted light.

The present invention has been made to solve such a problem, and an object of the present invention is to allow defects that are difficult to detect by seeing only a color difference in a captured image to be relatively easily detected.

Solution to Problem

To solve the above problem, a defect inspection system for a wood plank according to the present invention includes: a light for visible light that emits visible light for reflected light onto one side of a wood plank; a light for invisible light that emits invisible light for transmitted light onto another side of the wood plank that is opposite the one side; a capture device that generates an image by capturing the one side of the wood plank; and an image processing device that detects a plurality of kinds of defects of the wood plank by analyzing a captured image generated by the capture device, in which the defect inspection system discriminates the plurality of kinds of defects of the wood plank on the basis of a set that includes at least shading and shapes in an image based on the invisible light transmitted through the wood plank, and colors in an image based on the visible light reflected by the wood plank.

Advantageous Effects of Invention

According to the present invention configured as described above, even if a defect has a small color difference from a color of a normal part of a plank in an image captured while visible light is emitted, a difference between an amount of invisible light transmitted through the defective part and an amount of invisible light transmitted through the normal part allows difference of shading between the defective part and the normal part to appear in an image captured while invisible light is emitted. Therefore, it can be determined that a defect is in a part where the difference of shading exists. Further, a possible type of the defect can be determined on the basis of a set of a shape of the defective part that has been determined in a captured image based on invisible light, and colors of a corresponding part in a captured image based on visible light. Consequently, defects that are difficult to detect by seeing only a color difference in a captured image based on visible light become relatively easily detected.

BRIEF DESCRIPTION OF DRAWINGS

FIG. 3 is a flowchart that illustrates an example of operations of the defect inspection system for a wood plank according to the present embodiment.

DESCRIPTION OF EMBODIMENT

Figure 1:
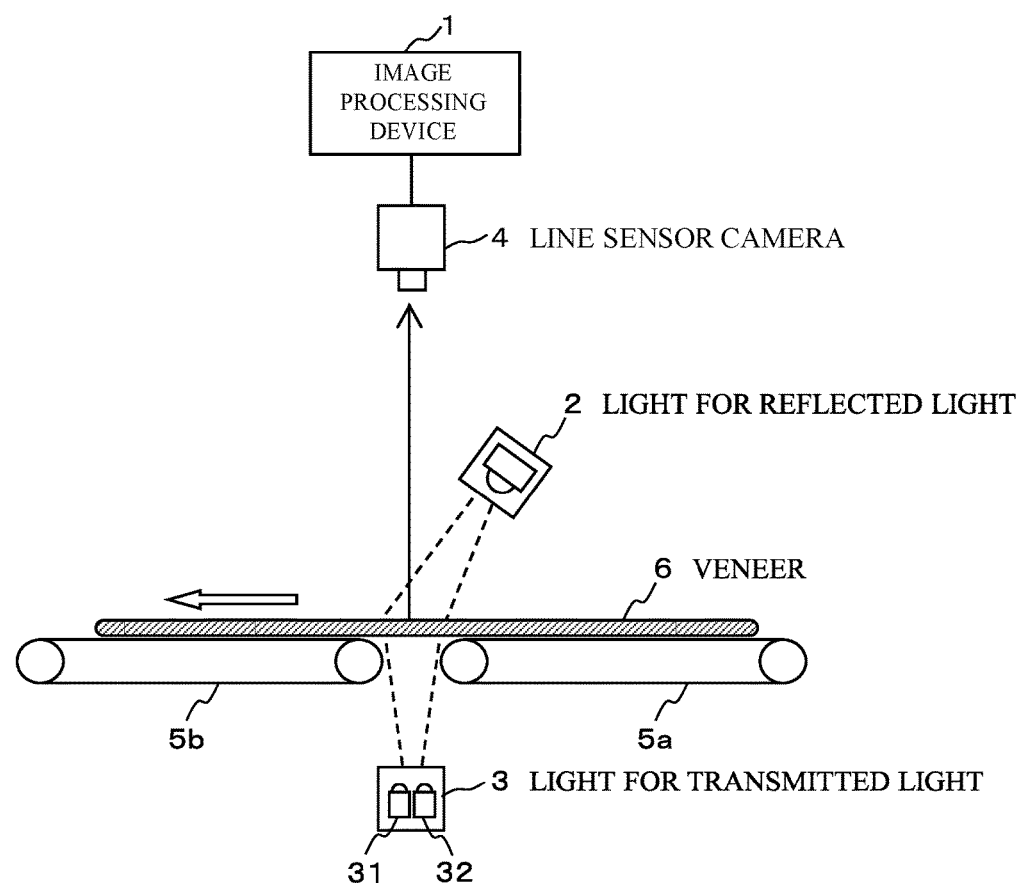
FIG. 1 is a diagram that illustrates an example of configuration of a defect inspection system for a wood plank according to a present embodiment.

Hereinafter, an embodiment of the present invention will be described with reference to the drawings. FIG. 1 is a diagram that illustrates an example of configuration of a defect inspection system for a wood plank according to the present embodiment. As illustrated in FIG. 1, the defect inspection system according to the present embodiment includes an image processing device 1, a light 2 for reflected light, a light 3 for transmitted light, and a line sensor camera 4 and detects a plurality of kinds of defects that exists in a veneer 6 conveyed by conveyor belts 5*a* and 5*b* (hereinafter simply referred to as the conveyor belts 5).

The light 2 for reflected light includes a light for visible light in the claims and emits visible light for reflected light onto one side (front side) of the veneer 6. For example, a white-light source, such as light-emitting diodes (LEDs), is used as the light for visible light. Hereinafter, visible light emitted by the light 2 for reflected light is referred to as "white visible light". The light 2 for reflected light extends like a line in a direction that is perpendicular to a direction in which the veneer 6 is conveyed (a width direction of the veneer 6) and emits white visible light in a belt-like shape onto the veneer 6.

The light 3 for transmitted light includes a second light 31 for visible light and a light 32 for invisible light in the claims. The second light 31 for visible light emits, onto another side (back side) opposite the one side of the veneer 6, visible light for transmitted light having a color that is easily discriminated from a color of reflected light that is from the light for visible light being the light 2 for reflected light and is reflected by the veneer 6. For example, a blue-light source or a green-light source, such as an LED, is used as the second light 31 for visible light. Hereinafter, visible light emitted by the second light 31 for visible light of the light 3 for transmitted light is referred to as "second visible light". The light 32 for invisible light emits invisible light for transmitted light onto the back side of the veneer 6. For example, a near-infrared light source, such as an LED, is used as the light 32 for invisible light. Hereinafter, invisible light emitted by the light 32 for invisible light of the light 3 for transmitted light is referred to as "near-infrared light". The light 3 for transmitted light (the second light 31 for visible light and the light 32 for invisible light) also extends like a line in a direction that is perpendicular to the direction in which the veneer 6 is conveyed (the width direction of the veneer 6) and emits second visible light and near-infrared light in a belt-like shape onto the veneer 6.

Here, as a wavelength band of the near-infrared light, an appropriate wavelength band with which the near-infrared light can be transmitted through the veneer 6 is used in relation to a thickness of the veneer 6. Preferably, the appropriate wavelength band is also used considering a sensitivity band of the line sensor camera 4. For example, if a thickness of the veneer 6 is approximately 6 mm, near-infrared light with a wavelength band of 750 to 1500 nm may be used. However, the wavelength band is not limited to 750 to 1500 nm.

The light 3 for transmitted light (the second light 31 for visible light and the light 32 for invisible light) is disposed at a position that is opposite a gap between the upstream conveyor belt 5*a* and the downstream conveyor belt 5*b* and emits invisible light (near-infrared light) and second visible light onto a back side of the veneer 6 from a back side of the conveyor belts 5 through the gap. On the other hand, the light 2 for reflected light is disposed at a position slightly upstream (or downstream) of the gap between the upstream conveyor belt 5*a* and the downstream conveyor belt 5*b*, and diagonally emits white visible light from a front side of the conveyor belts 5 onto an area of a front side opposite an area of the back side of the veneer 6 onto which the near-infrared light and the second visible light are emitted.

The line sensor camera 4 corresponds to a capture device in the claims and generates images by capturing the front sides of the veneers 6 in color. The line sensor camera 4 is disposed at a position opposite the light 3 for transmitted light across the gap between the upstream conveyor belt 5*a* and the downstream conveyor belt 5*b*, extends in a direction that is perpendicular to the direction in which the veneer 6 is conveyed (the width direction of the veneer 6), and captures an image of the veneer 6 in a line-shape. When the veneer 6 is conveyed on the conveyor belts 5, the line sensor camera 4 repeatedly generates one line of image every predetermined sampling times from one end side of the veneer 6 to the other end side of the veneer 6 in the direction in which the veneer 6 is conveyed and successively outputs the lines of images to the image processing device 1.

The line sensor camera 4 includes a photodetector that is sensitive to white visible light emitted by the light 2 for reflected light and second visible light emitted by the second light 31 for visible light of the light 3 for transmitted light, and a photodetector that is sensitive to near-infrared light emitted by the light 32 for invisible light of the light 3 for transmitted light. The line sensor camera 4 receives reflected light of white visible light that has been emitted by the light 2 for reflected light and reflected by the veneer 6, and transmitted light of near-infrared light and second visible light that have been emitted by the light 3 for transmitted light (the second light 31 for visible light and the light 32 for invisible light) and transmitted through the veneer 6. The line sensor camera 4 photoelectrically converts the reflected light and the transmitted light to generate one line of captured image of the veneer 6.

Here, the line sensor camera 4 generates an image based on the reflected light of the white visible light and the transmitted light of the second visible light (hereinafter referred to as the visible-light image), and an image based on the transmitted light of the near-infrared light (hereinafter referred to as the infrared-transmitted-light image). If the veneer 6 has a hole that penetrates substantially vertically from the back side to the front side, the second visible light is transmitted through the through hole, and the second visible light transmitted through the through hole forms an image as part of the visible-light image. On the other hand, the near-infrared light is transmitted through the whole veneer 6 including a part that includes the through hole described above and a part that does not include the through hole, and the near-infrared light forms the infrared-transmitted-light image. At this time, a part of the veneer 6 that has a thickness, a fiber density, a fiber direction, and the like different from those around the part appears white or black.

Note that hereinafter, part of a visible-light image based on transmitted light of second visible light is referred to as a second visible light image, and the other part of the visible-light image based on reflected light of white visible light is referred to as a white-reflected-light image. Strictly speaking, white visible light may be reflected to the line sensor camera 4 by a part that transmits second visible light. For convenience of explanation, however, part of an image that does not include the second visible light image (part that does not transmit second visible light) is referred to as the white-reflected-light image.

The image processing device 1 synthesizes (combines) a plurality of lines of the captured images successively output from the line sensor camera 4 every predetermined sampling times to generate a visible-light image of the whole veneer 6 and an infrared-transmitted-light image of the whole veneer 6. Then the image processing device 1 analyzes the visible-light image and the infrared-transmitted-light image that have been generated. Consequently, the image processing device 1 detects a plurality of kinds of defects that exists in the veneer 6.

Figure 2:
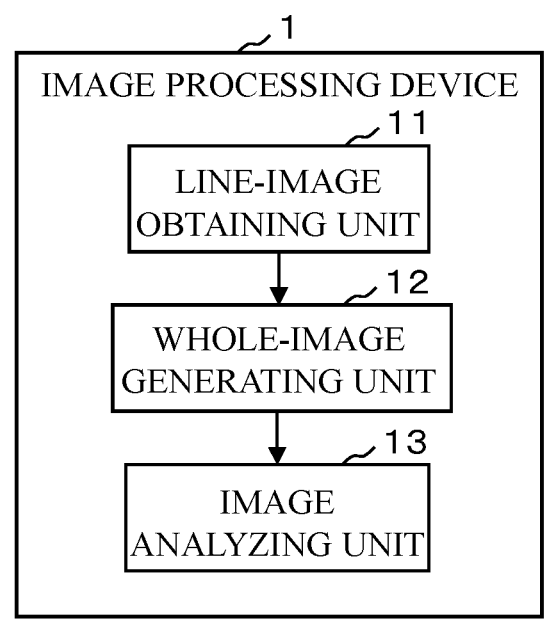
FIG. 2 is a block diagram that illustrates an example of functional configuration of an image processing device according to the present embodiment.

FIG. 2 is a block diagram that illustrates an example of functional configuration of the image processing device 1. As illustrated in FIG. 2, the image processing device 1 includes, as a functional configuration, a line-image obtaining unit 11, a whole-image generating unit 12, and an image analyzing unit 13. Each of these functional blocks 11 to 13 may be configured with hardware, a digital signal processor (DSP), or software. If each of the functional blocks 11 to 13 is configured with, for example, software, each of the functional blocks 11 to 13 is configured with a central processing unit (CPU), a random-access memory (RAM), a read-only memory (ROM), and the like of a computer, and is implemented by running programs stored in a storage medium, such as the RAM, the ROM, a hard disk, or a semiconductor memory.

The line-image obtaining unit 11 successively obtains one line of captured image generated by the line sensor camera 4 every predetermined sampling times. The whole-image generating unit 12 generates an image of the whole veneer 6 by synthesizing (combining) a plurality of lines of the captured images obtained by the line-image obtaining unit 11. At this time, the whole-image generating unit 12 generates a visible-light image including a white-reflected-light image and a second visible light image, and generates an infrared-transmitted-light image.

The image analyzing unit 13 analyzes the images of the whole veneer 6 generated by the whole-image generating unit 12, and thus detects a plurality of kinds of defects of the veneer 6. Here, the image analyzing unit 13 discriminates a plurality of kinds of defects of the veneer 6 on the basis of a set of colors, shapes, and patterns in the white-reflected-light image, colors and shapes in the second visible light image, and shading and shapes in the infrared-transmitted-light image. The image analyzing unit 13 detects defects of the veneer 6, such as a worm hole, a live knot, a dead knot, an opening crack, a non-opening crack, a bark pocket, a resin pocket, reaction wood, discolored part due to staining fungi and the like, and clogging of a blade. The discolored part due to staining fungi and the like is a concept including a part that has been discolored due to staining fungi such as a part of wood that has been discolored by staining fungi and a part to which discolored fungi adheres. The discolored part due to staining fungi and the like is, for example, a part of wood that has been discolored from blue to black due to blue mold or black mold caused by blue staining fungi. Hereinafter, the discolored part due to staining fungi and the like is referred to as "the discolored part".

Among the various defects, the opening crack, the bark pocket, the resin pocket, and the clogging of a blade can be discriminated to some degree, without the infrared-transmitted-light image, on the basis of colors, shapes, patterns, and the like in the visible-light image (the white-reflected-light image and the second visible light image).

The opening crack is a type of crack that extends through the veneer 6 from the back side of the veneer 6 to the front side of the veneer 6 along an optical axis of second visible light in a thickness direction, and has openings. The opening crack transmits second visible light emitted by the second light 31 for visible light of the light 3 for transmitted light. Therefore, a color difference between a defective part of the opening crack (a second visible light image) and a normal part of peripheral wood (a white-reflected-light image) is large, and the color difference allows existence of the defect to be detected. Further, it is determined that the defect is a "crack" on the basis of a shape of the defective part that generates the color difference.

The bark pocket is a defect that is likely to have a color of dark brown or black. Therefore, if a color difference between a defective part of a bark pocket and a normal part of peripheral wood is large in a white-reflected-light image based on white visible light emitted by the light 2 for reflected light, the color difference allows existence of a defect to be detected. Further, if a pattern such as grain of the defective part that generates the color difference is characteristic of a bark pocket, it is determined that the defect is a "bark pocket".

The resin pocket is a defect of a hole that contains resin. The resin pocket is often a black discoloration. Therefore, if a color difference between a defective part of a resin pocket and a normal part of peripheral wood is large in a white-reflected-light image, the color difference allows existence of a defect to be detected. Further, if a resin pocket extends through in the thickness direction, the resin pocket transmits second visible light emitted by the second light 31 for visible light of the light 3 for transmitted light. At this time, if a color difference between the defective part (a second visible light image) and a normal part of peripheral wood (a white-reflected-light image) is large (if part around the hole has not been blackened), the color difference allows existence of a defect to be detected. Further, it is determined that the defect may be a "resin pocket", a "bark pocket" or a black "knot" on the basis of a color of the defective part that generates the color difference.

The clogging of a blade is a defect where a thickness of a plank is different from a thickness of the plank around the clogging of a blade, and a grain pattern is not continuous. Therefore, if it is apparent that a grain pattern is not continuous in a white-reflected-light image based on white visible light emitted by the light 2 for reflected light, it is determined that there is a defect of "clogging of a blade".

In contrast to the above defects, for the worm hole, the live knot, the dead knot, the non-opening crack, the reaction wood, and the discolored part, the image analyzing unit 13 discriminates a plurality of kinds of defects of the veneer 6 on the basis of a set of shading and shapes in an infrared-transmitted-light image based on transmitted light of near-infrared light emitted from the light 32 for invisible light of the light 3 for transmitted light, and colors in a white-reflected-light image based on reflected light of white visible light emitted from the light 2 for reflected light.

The worm hole is a hole formed by damage by worms. The worm hole may be a through hole that extends through the veneer 6 in the thickness direction or a blind hole that does not extend through the veneer 6 in the thickness direction. If a worm hole is a blind hole, the worm hole does not transmit second visible light from the second light 31 for visible light of the light 3 for transmitted light, the worm hole is not detected on the basis of a second visible light image. Further, a worm hole is difficult to detect on the basis of only a white-reflected-light image based on white visible light from the light 2 for reflected light unless a discoloration of a worm-eaten part, for example, causes an apparent difference between a color of the worm-eaten part and a color of peripheral wood. A worm hole filled with feces of the worm is more difficult to detect.

Near-infrared light emitted by the light 32 for invisible light of the light 3 for transmitted light is transmitted from a back side to the front side of the veneer 6 including a normal part and a defective part by contrast. Here, a worm hole that is a blind hole or a worm hole that is blocked with feces is likely to be white in an infrared-transmitted-light image due to a difference in a transmission amount of near-infrared light from a normal part of peripheral wood.

Therefore, the image analyzing unit 13 can detect existence of a defect in a white part in an infrared-transmitted-light image. Further, if a shape of the white part is an irregular elongated hole, or an elongated hole that is perpendicular to fibers, it is determined that the defect is a "worm hole". If the white part has a shape like a circle, the image analyzing unit 13 can determine whether the white part is a worm hole, a loose knot, or a pinhole considering a color and a shape of a part of a white-reflected-light image that corresponds to the white part. Note that some worms have a characteristic of generating mold around a part damaged by the worms. In this case, mold grows around a worm hole, and the mold part is likely to be black in an infrared-transmitted-light image. Therefore, it is determined whether or not a hole is a worm hole by detecting such a state.

The live knot is a type of knot in which peripheral wood and fibers are continuous. Since a color of a live knot is similar to a color of wood of the veneer 6, the boundary is often not apparent, and the live knot is often difficult to detect on the basis of only a visible-light image. A part where a live knot exists is white in an infrared-transmitted-light image by contrast. Therefore, the image analyzing unit 13 can detect existence of a defect in a white part in an infrared-transmitted-light image. If the white part is a live knot, the white part has a shape like a circle. Therefore, the image analyzing unit 13 determines whether the white part is a worm hole or a live knot considering a color and a shape of a part of a white-reflected-light image that corresponds to the white part.

The dead knot is a type of knot in which peripheral wood and fibers are not continuous and is more likely to be black than the live knot is. Therefore, in many cases, a boundary between a dead knot and peripheral wood is relatively more apparent than a boundary between a live knot and peripheral wood, and the dead knot may be detectable on the basis of a visible-light image. However, the dead knot is difficult to detect if a difference in a color between the dead knot and the peripheral wood is small, such as the case of the veneer 6 made of wood the whole of which is blackish. A part where a dead knot exists is white in an infrared-transmitted-light image by contrast. Therefore, the image analyzing unit 13 can detect existence of a defect in a white part in an infrared-transmitted-light image. A dead knot also has a shape like a circle. However, since a dead knot is often black in a white-reflected-light image, a dead knot can be determined on the basis of a color.

The non-opening crack is a crack that penetrates the veneer 6 from the back side to the front side but does not open along an optical axis of second visible light, or a crack that does not penetrate the veneer 6 from the back side to the front side. The non-opening crack does not transmit second visible light from the second light 31 for visible light of the light 3 for transmitted light. Therefore, the non-opening crack is not detected on the basis of a second visible light image. Further, the non-opening crack has a small difference from a normal part of peripheral wood in both a color and a pattern of the color (pattern such as grain). Therefore, the non-opening crack is difficult to detect on the basis of only a white-reflected-light image. A part where the non-opening crack exists is white in an infrared-transmitted-light image by contrast due to an influence of an insufficient thickness of the plank that is chipped and an influence of light that leaks from a space where the crack allows near-infrared light to be likely to be scattered. Therefore, the image analyzing unit 13 can detect existence of a defect in a white part in an infrared-transmitted-light image. Further, it is determined that the defect is a "crack" on the basis of a shape of the white part.

The reaction wood is a strong part where density of wood fibers is high. Minute cracks may be generated since a density of the reaction wood is different from a density of peripheral normal wood. However, since the reaction wood does not have a characteristic color, the reaction wood is often difficult to detect on the basis of only a visible-light image. In an infrared-transmitted-light image, by contrast, the reaction wood is black if a density of wood fibers is simply high. Therefore, the image analyzing unit 13 can detect existence of a defect in a black part in an infrared-transmitted-light image. Further, on the basis of a shape of the black part and a color of a part that corresponds to the black part in a white-reflected-light image, the black part can be discriminated from discolored part (as an example, a part that has been discolored black due to blue mold or black mold) that is also black in an infrared-transmitted-light image, and it can be determined that the defect is "reaction wood". Note that a part that has clogging of a blade may be black in an infrared-transmitted-light image. However, the clogging of a blade can be discriminated from the reaction wood on the basis of a shape of the part and a color in a white-reflected-light image.

The discolored part does not have a characteristic shape. The discolored part has been detected as a discoloration in a white-reflected-light image. However, the blue mold has a color, for example, from black to blue black, and is difficult to discriminate from a stain. If the veneer 6 is made of a material that has a shade of black, existence of blue mold is difficult to detect. Further, light-colored discolored part is also difficult to detect from a white-reflected-light image. A part that has the discolored part is black in an infrared-transmitted-light image by contrast. Therefore, the image analyzing unit 13 can detect existence of a defect in a black part in an infrared-transmitted-light image. Further, it is determined that the defect is "the discolored part" on the basis of a shape of the black part that is not a shape characteristic to reaction wood or clogging of a blade, or on the basis of a color of a corresponding part in a white-reflected-light image As described above, the opening crack, the bark pocket, the resin pocket, and the clogging of a blade can be discriminated to some degree, without an infrared-transmitted-light image, on the basis of colors, shapes, patterns, and the like in a visible-light image. However, these defective parts appear white or black in an infrared-transmitted-light image. Thus, the parts that appear white or black may be extracted by analyzing an infrared-transmitted-light image, and then types of defects may be discriminated by analyzing colors, shapes, patterns, and the like of corresponding parts in a visible-light image.

A resin pocket may be especially difficult to detect by analyzing only a visible-light image if the resin pocket contains much resin, is only a discoloration, and is a blind hole. Clogging of a blade may also be difficult to detect by analyzing only a visible-light image if a color of the clogging of the blade is not much different from a color of a part around the clogging of the blade. In an infrared-transmitted-light image, a part where a resin pocket exists is white, and a part where clogging of a blade exists is white or black by contrast. Therefore, existence of these defects can be detected. Further, types of the defects can be discriminated on the basis of a shape of the white or black part and colors of corresponding parts in a visible-light image.

FIG. 3 is a flowchart that illustrates an example of operations of the defect inspection system for a veneer according to the present embodiment, constituted as described above. The flowchart illustrated in FIG. 3 starts when the defect inspection system is operated to instruct the defect inspection system to start operations.

Note that if the defect inspection system is instructed to start operations, a plurality of veneers 6 is successively conveyed on the conveyor belts 5, and each of the veneers 6 is successively inspected to detect defects. However, FIG. 3 illustrates an example of operations where one veneer 6 is dealt with.

First, the line sensor camera 4 captures one line of image of part of the veneer 6 in the width direction of the veneer 6 while white visible light is emitted onto the front side of the veneer 6 from the light 2 for reflected light, and second visible light and near-infrared light are emitted onto the back side of the veneer 6 from the light 3 for transmitted light (the second light 31 for visible light and the light 32 for invisible light). The line sensor camera 4 outputs the obtained captured image (a visible-light image and an infrared-transmitted-light image) into the image processing device 1 (step S1).

The line-image obtaining unit 11 of the image processing device 1 obtains the one line of captured image output from the line sensor camera 4 (step S2). Further, the whole-image generating unit 12 further combines the one line of captured image obtained by the line-image obtaining unit 11 with a captured image that has been generated so far by synthesizing (combining) (step S3). Then the whole-image generating unit 12 determines whether or not an image of the whole veneer 6 has been generated (step S4).

For example, if a line-shaped edge due to an apparent difference in color in the width direction of the veneer 6 is detected in the synthesized captured image, it is determined that an image of the whole veneer 6 has been generated. If an image of the whole veneer 6 has not been generated, the process returns to step S1. Then the process from steps S1 to S4 is repeated every predetermined sampling times.

On the other hand, if the whole-image generating unit 12 determines that an image of the whole veneer 6 has been generated, the image analyzing unit 13 analyzes the image of the whole veneer 6 generated by the whole-image generating unit 12 (step S5). Here, the image analyzing unit 13 analyzes colors, shapes, and patterns in a white-reflected-light image, colors and shapes in a second visible light image, and shading and shapes in an infrared-transmitted-light image. Consequently, a plurality of kinds of defects that exists in the veneer 6 is detected (step S6). The result is displayed on a screen of the defect inspection system.

As described in detail above, a light for visible light (the light 2 for reflected light) that emits white visible light for reflected light onto the front side of the veneer 6, a light 32 for invisible light (part of the light 3 for transmitted light) that emits near-infrared light for transmitted light onto the back side of the veneer 6, the line sensor camera 4 that generates an image by capturing the front side of the veneer 6, and the image processing device 1 (the image analyzing unit 13) that detects a plurality of kinds of defects of the veneer 6 by analyzing a captured image generated by the line sensor camera 4 are provided in the present embodiment. In the present embodiment, defects, such as a worm hole, a live knot, a dead knot, a non-opening crack, reaction wood, discolored part due to staining fungi and the like, and the like, are discriminated on the basis of a set of shading and shapes in an infrared-transmitted-light image based on the transmitted light, and colors in a white-reflected-light image based on the reflected light.

According to the present embodiment configured as described above, even if a defect has a small color difference from a color of a normal part of a plank in a white-reflected-light image captured while white visible light is emitted, a difference between an amount of near-infrared light transmitted through the defective part and an amount of near-infrared light transmitted through the normal part allows difference of shading between the defective part and the normal part to appear in an infrared-transmitted-light image. Therefore, it is determined that a defect is in a part where the difference of shading exists. Further, a possible type of the defect can be determined on the basis of a set of a shape of the defective part that has been determined in the infrared-transmitted-light image, and colors of a corresponding part in the white-reflected-light image. Consequently, defects that are difficult to detect by seeing only a color difference in a white-reflected-light image become relatively easily detected. Defects, such as a worm hole, a live knot, a dead knot, a non-opening crack, reaction wood, and discolored part due to staining fungi and the like, especially become more easily detected.

Further, in the present embodiment, the second light 31 for visible light (part of the light 3 for transmitted light) that emits second visible light for transmitted light onto the back side of the veneer 6 is also provided so that a plurality of kinds of defects of the veneer 6 is discriminated on the basis of a set of colors, shapes, and patterns in a white-reflected-light image, colors and shapes in a second visible light image, and shading and shapes in an infrared-transmitted-light image. Consequently, it is possible to easily detect a plurality of kinds of defects such as a worm hole, a live knot, a dead knot, an opening crack, a non-opening crack, a bark pocket, a resin pocket, reaction wood, discolored part due to staining fungi and the like, and clogging of a blade, including defects that can be detected on the basis of only a visible-light image. A defect that can be detected without a second visible light image can also be more easily detected by analyzing the second visible light image if the defect penetrates the veneer 6 from the back side to the front side substantially vertically.

Note that in the above embodiment, an example in which the line sensor camera 4 is used as a capture device, the line sensor camera 4 includes a photodetector sensitive to visible light and a photodetector sensitive to near-infrared light, and a visible-light image and an infrared-transmitted-light image are separately generated is described. However, the present invention is not limited to the example. For example, a capture device that includes a photodetector sensitive to a visible range to a near-infrared range may be used to generate a captured image, and the captured image may be divided into a visible-light image and an infrared-transmitted-light image.

Further, in the above embodiment, an example in which a visible-light image that includes a white-reflected-light image and a second visible light image is analyzed is described. However, the present invention is not limited to the example.

For example, a white-reflected-light image and a second visible light image may be separated from a visible-light image. The white-reflected-light image and the second visible light image may be separately analyzed.

Further, in the above embodiment, an example in which the line sensor camera 4 is used as a capture device is described. However, the present invention is not limited to the example. For example, an area sensor camera that can capture the whole veneer 6 in one image may be used. In this case, the light 2 for reflected light and the light 3 for transmitted light (the second light 31 for visible light and the light 32 for invisible light) emit white visible light, second visible light, and near-infrared light in an area shape onto the whole veneer 6.

Further, in the above embodiment, an example in which a white-light source is used as the light for visible light, and a blue-light source or a green-light source is used as the second light 31 for visible light is described. However, the present invention is not limited to the example. Another set of colors may be used if a color of a light for reflected light and a color of a light for transmitted light can be discriminated from each other.

Further, in the above embodiment, an example in which the second light 31 for visible light that emits second visible light for transmitted light is provided is described. However, the second light 31 for visible light may be eliminated. Even if the second light 31 for visible light is eliminated, defects, such as a worm hole, a live knot, a dead knot, a non-opening crack, reaction wood, and discolored part due to staining fungi and the like, that are difficult to detect by seeing only a color difference in a visible-light image become relatively easily detected.

Further, in the above embodiment, an example in which a near-infrared light source is used as the light 32 for invisible light is described. However, the present invention is not limited to the example. A wavelength band that is transmitted through the veneer 6, and corresponds to a band to which a photodetector of the line sensor camera 4 is sensitive may be possible. For example, mid-infrared light, far-infrared light, terahertz radiation, ultraviolet light, and X-rays may be used.

Further, in the above embodiment, an example in which defects that exist in the veneer 6 are detected is described. However, the present invention is not limited to the example. For example, defects of other wood planks, such as a sawn timber, may be detected.

Each of the above embodiments only shows one concrete example of implementation of the present invention, and a technical scope of the present invention should not be interpreted in a limited manner by the example. That is to say, the present invention can be implemented in various forms without departing from a gist of the present invention or main characteristics of the present invention.

REFERENCE SIGNS LIST

1 Image processing device
2 Light for reflected light (light for visible light)
3 Light for transmitted light
31 Second light for visible light
32 Light for invisible light
4 Line sensor camera (capture device)
11 Line-image obtaining unit
12 Whole-image generating unit
13 Image analyzing unit

The invention claimed is:

1. A defect inspection system for a wood plank, the defect inspection system comprising:
a light for visible light that emits visible light for reflected light onto one side of a wood plank;
a light for invisible light that emits invisible light for transmitted light onto another side of the wood plank that is opposite the one side;
a capture device that generates a visible light image of the visible light reflected by the one side of the wood plank and an invisible light image of invisible light transmitting through the one side of the wood plank; and
an image processing device that detects a plurality of kinds of surface defects of the wood plank by analyzing the visible and invisible light images generated by the capture device, wherein
the image processing device being programmed to determine the presence and type of any of the plurality of kinds of defects in the wood plank on a basis of the characteristics of a set that includes shading and shapes that reflects the characteristics of transmitted light for each type of defect of the wood plank in the invisible light image, and colors, shapes and patterns that reflects the characteristics of reflected light for each type of defect of the wood plank in the visible light image.

2. The defect inspection system for a wood plank according to claim 1, wherein the light for visible light includes a white-light source, and the light for invisible light includes a near-infrared light source.

3. The defect inspection system for a wood plank according to claim 1, further comprising a second light for visible light that emits visible light for transmitted light onto another side of the wood plank, the visible light for transmitted light having a color that is easily discriminated from a color of reflected light that is from the light for visible light and is reflected by the wood plank.

4. The defect inspection system for a wood plank according to claim 3, wherein the light for visible light includes a white-light source, the light for invisible light includes a near-infrared light source, and the second light for visible light includes a light source that has a color that is different from a color of the white-light source.

5. A defect inspection method for a wood plank, the method comprising:
generating a visible light image and an invisible light image by capturing one side of a wood plank with a capture device while emitting visible light for reflected light onto the one side of the wood plank from a light for visible light, and emitting invisible light for transmitted light onto another side of the wood plank that is opposite the one side from a light for invisible light;
analyzing the captured visible and invisible light images generated by the capture device for characteristics of a plurality of kinds of defects in the wood plank; and
determining, the presence and type of any of the plurality of kinds of defects in the wood plank on a basis of the characteristics of a set that includes shading and shapes that reflects the characteristics of transmitted light for each type of defect of the wood plank in the invisible light image, and colors, shapes and patterns that reflects the characteristics of reflected light for each type of defect of the wood plank in the visible light image.

6. The defect inspection method for a wood plank according to claim 5, wherein the light for invisible light includes a near-infrared light source.

7. The defect inspection system of claim 1, wherein the image processing device determines a defect in the wood plank is a worm hole from a white part in the invisible light image, the white part having a shape of an irregular elongated hole, or an elongated hole that is perpendicular to fibers of the wood plank.

8. The defect inspection system of claim 1, wherein the image processing device determines whether a white part having a circular shape in the invisible light image is a worm hole, a loose knot, a pinhole, or a live knot on the basis of a color and a shape of a part of the visible light image that corresponds to the white part.

9. The defect inspection system of claim 1, wherein the image processing device determines a white part having a circular shape in the invisible light image is a dead knot on the basis of a color of a part of the visible light image that corresponds to the white part.

10. The defect inspection system of claim 1, wherein the image processing device determines a defect in the wood plank is a non-opening crack from a white part having a shape from light scattered by the crack in the invisible light image.

11. The defect inspection system of claim 1, wherein the image processing device determines a black part in the invisible light image is reaction wood on the basis of a shape of the black part and a color of a part of the visible light image that corresponds to the black part.

12. The defect inspection system of claim 1, wherein the image processing device determines a defect in the wood is a discolored part from a black part in the invisible light image in combination with a color of a part of the visible light image that corresponds to the black part of the invisible light image.

13. The defect inspection method of claim 5, wherein the determining determines a defect in the wood plank is a worm hole from a white part in the invisible light image, the white part having a shape of an irregular elongated hole or an elongated hole that is perpendicular to fibers of the wood plank.

14. The defect inspection method of claim 5, wherein the determining determines whether a white area having a circular shape in the invisible light image is a worm hole, a loose knot, a pinhole, or a live knot on the basis of a color and a shape of a part of the visible light image that corresponds to the white part.

15. The defect inspection method of claim 5, wherein the determining determines a white part having a circular shape in the invisible light image is a dead knot on the basis of a color of a part of the visible light image that corresponds to the white part.

16. The defect inspection method of claim 5, wherein the determining determines a defect in the wood plank is a non-opening crack from a white part having a shape from light scattered by the crack in the invisible light image.

17. The defect inspection method of claim 5, wherein the determining determines a black part in the invisible light image is reaction wood on the basis of a shape of the black part and a color of a part of the visible light image that corresponds to the black part.

18. The defect inspection method of claim 5, wherein the determining determines a defect in the wood is a discolored part from a black part in the invisible light image in combination with a color of a part of the visible light image that corresponds to the black part of the invisible image.

* * * * *